US00PP17563P2

(12) United States Plant Patent
Smith

(10) Patent No.: US PP17,563 P2
(45) Date of Patent: Apr. 3, 2007

(54) ***HIBISCUS* PLANT NAMED 'SPLASH YOPINOT NOIR'**

(50) Latin Name: *Hisbiscus moscheutos*
Varietal Denomination: Splash Yopinot Noir

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 39 days.

(21) Appl. No.: 11/177,993

(22) Filed: Jul. 8, 2005

(51) Int. Cl.
*A01H 5/00* (2006.01)

(52) U.S. Cl. ..... Plt./257
(58) Field of Classification Search ..... Plt./257
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'Splash Yopinot Noir', characterized by its upright and outwardly spreading plant habit; freely branching and moderately vigorous growth habit; early flowering habit; large dark red-colored flowers; and excellent garden performance.

2 Drawing Sheets

Botanical designation: *Hibiscus moscheutos.*
Cultivar denomination: 'Splash Yopinot Noir'.

CROSS-REFERENCE TO RELATED APPLICATIONS

Hibiscus Plant Named 'Carafe Yobordeaux'; Mark A. Smith, applicant; disclosed in a U.S. Plant patent application Ser. No. 11/178,272 filed concurrently.

BACKGROUND OF THE INVENTION

The present invention relates to a new and distinct cultivar of *Hibiscus,* botanically known as *Hibiscus moscheutos,* and hereinafter referred to by the name 'Splash Yopinot Noir'.

The new *Hibiscus* is a product of a planned breeding program conducted by the Inventor in Alva, Fla. The objective of the breeding program is to create new freely-branching and *Hibiscus* cultivars with a compact plant habit and attractive flower coloration.

The new *Hibiscus* originated from a cross-pollination made by the Inventor in Alva, Fla. during the summer of 2001, of the *Hibiscus moscheutos* cultivar Carafe Yobordeaux, disclosed in a U.S. Plant Patent application filed concurrently, as the female, or seed, parent with the *Hibiscus moscheutos* cultivar Disco Belle Pink, not patented, as the male, or pollen, parent. The cultivar Splash Yopinot Noir was discovered and selected by the Inventor as a flowering plant within the progeny of the stated cross-pollination in a controlled environment in Alva, Fla. in April, 2002.

Asexual reproduction of the new *Hibiscus* by vegetative terminal cuttings in a controlled environment in Alva, Fla. since May, 2002, has shown that the unique features of this new *Hibiscus* are stable and reproduced true to type in successive generations.

SUMMARY OF THE INVENTION

The cultivar Splash Yopinot Noir has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Splash Yopinot Noir'. These characteristics in combination distinguish 'Splash Yopinot Noir' as a new and distinct cultivar:

1. Upright and outwardly spreading plant habit.
2. Freely branching and moderately vigorous growth habit.
3. Early flowering habit.
4. Large dark red-colored flowers.
5. Excellent garden performance.

Plants of the new *Hibiscus* can be compared to plants of the female parent, the cultivar Carafe Yobordeaux. Plants of the new *Hibiscus* differ from plants of the unnamed whole plant mutation of the cultivar Carafe Yobordeaux in the following characteristics:

1. Plants of the new *Hibiscus* flower about two to three days earlier than plants of the cultivar Carafe Yobordeaux.
2. Plants of the new *Hibiscus* have darker red-colored flowers than plants of the cultivar Carafe Yobordeaux.

Plants of the new *Hibiscus* can be compared to plants of the male parent, the cultivar Disco Belle Pink. Plants of the new *Hibiscus* differ from plants of the cultivar Disco Belle Pink in the following characteristics:

1. Plants of the new *Hibiscus* are shorter and fuller than plants of the cultivar Disco Belle Pink.
2. Plants of the new *Hibiscus* and the cultivar Disco Belle Pink differ in flower coloration as plants of the cultivar Disco Belle Pink have white-colored flowers with pink-colored margins.

Plants of the new *Hibiscus* can be compared to plants of the *Hibiscus* cultivar Disco Belle Red, not patented. In side-by-side comparisons conducted in Alva, Fla., plants of the new *Hibiscus* differed from plants of the cultivar Disco Belle Red in the following characteristics:

1. Plants of the new *Hibiscus* were taller and fuller than plants of the cultivar Disco Belle Red.

2. Plants of the new *Hibiscus* flowered about four days later than plants of the cultivar Disco Belle Red.
3. Plants of the new *Hibiscus* had larger flowers than plants of the cultivar Disco Belle Red.
4. Plants of the new *Hibiscus* had darker red-colored flowers than plants of the cultivar Disco Belle Red.

Plants of the new *Hibiscus* can also be compared to plants of the *Hibiscus* cultivar Luna Red, not patented. In side-by-side comparisons conducted in Alva, Fla., plants of the new *Hibiscus* flowered about three days earlier than plants of the cultivar Luna Red.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph on the first sheet comprises a side perspective view of a typical flowering plant of 'Splash Yopinot Noir' grown in an outdoor nursery in Alva, Fla. for about six months.

The photograph on the second sheet comprises a close-up view of a typical flower of 'Splash Yopinot Noir'.

DETAILED BOTANICAL DESCRIPTION

The following observations, measurements and values describe plants grown in Alva, Fla. in one-gallon containers in a polypropylene-covered shadehouse during the summer and under conditions which closely approximate commercial production. During the production of the plants, day temperatures ranged from 29° C. to 32° C. and night temperatures ranged from 21° C. to 24° C. Plants were pinched about one month after planting. The description was taken about two months after the pinch. In the description, color references are made to The Royal Horticultural Society Colour Chart, 1995 Edition, except where general terms of ordinary dictionary significance are used.

Botanical classification: *Hibiscus moscheutos* cultivar Splash Yopinot Noir.

Parentage:

*Female or seed parent.*—*Hibiscus moscheutos* cultivar Carafe Yobordeaux, disclosed in a U.S. Plant patent application filed concurrently.

*Male or pollen parent.*—*Hibiscus moscheutos* cultivar Disco Belle Pink, not patented.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick, fibrous; white in color.

*Rooting habit.*—Freely branching.

Plant description:

*Plant form and growth habit.*—Perennial shrub; upright and outwardly spreading plant habit. Moderately vigorous growth habit.

*Branching habit.*—Freely branching, lateral branches potentially forming at every node.

*Plant height.*—About 30 cm.

*Plant diameter* (*area of spread*).—About 40.5 cm.

*Lateral branch description.*—Length: About 21 cm. Diameter: About 5 mm. Internode length: About 2.2 cm. Texture: Smooth, glabrous. Color: 146A.

*Foliage description.*—Arrangement: Alternate, simple. Length: About 10.1 cm. Width: About 7.5 cm. Shape: Cordate to ovate. Apex: Acute; narrowly tapering. Base: Cordate. Margin: Crenate; undulate. Texture, upper and lower surfaces: Smooth, glabrous. Venation pattern: Palmate. Color: Developing foliage, upper surface: Close to 147A. Developing foliage, lower surface: Close to 147B. Fully expanded foliage, upper surface: Darker green than 147A. Fully expanded foliage, lower surface: Close to 147B. Venation, upper surface: Towards the margins, 147A; towards the base, close to 187A. Venation, lower surface: Close to 144B. Petiole: Length: About 3.9 cm. Diameter: About 3 mm. Texture, upper and lower surfaces: Smooth, glabrous. Color, upper surface: Close to 146A to 146B overlain with 187A. Color, lower surface: Close to 146A to 146B.

Flower description:

*Flower arrangement.*—Flowers develop at axillary leaf axils; typically one or two flowers per axil. Flower face upright to outward.

*Flower appearance.*—Rotate dark red-colored flowers. Flowers are open for about two days. Flowers persistent.

*Natural flowering season.*—Usually spring and summer or during periods of warm weather.

*Flower diameter.*—About 12.1 cm.

*Flower length* (*height*).—About 2.8 cm.

*Flower bud.*—Length: About 1.75 cm. Diameter: About 1.4 cm. Shape: Ovoid. Color: Close to 147B.

*Petals.*—Quantity/arrangement: Corolla consists of five petals; petals imbricate. Length: About 6 cm. Width: About 6.5 cm. Shape: Roughly orbicular. Apex: Rounded; undulate. Base: Attenuate. Margin: Entire to slightly crenate; undulate. Texture, upper and lower surfaces: Smooth, glabrous; satiny; rugose. Color: When opening and fully opened, upper surface: Close to 46A to 53A; color becoming closer to 60A with development; towards the base, close to 53A; venation, similar to lamina. When opening and fully opened, lower surface: Close to 53A; venation, similar to lamina.

*Sepals.*—Quantity/arrangement: Five sepals fused into a tubular calyx. Length: About 1.9 cm. Width: About 1.3 cm. Shape: Oblong. Apex: Cuspidate. Margin: Entire. Texture, upper surface: Smooth, glabrous. Texture, lower surface: Slightly pubescent. Color, upper surface: Close to 146A. Color, lower surface: Close to 147B.

*Bracts.*—Quantity/arrangement: About ten in a single whorl. Length: About 1.5 cm. Width: About 3 mm. Shape: Lanceolate. Apex: Sharply acute. Margin: Entire. Texture, upper and lower surfaces: Slightly pubescent. Color, upper surface: Close to 146A. Color, lower surface: Between 146A and 147A.

*Peduncles.*—Length: About 1.3 cm. Diameter: About 2 mm. Angle: Straight to slightly bent. Strength: Strong, flexible. Texture: Smooth, glabrous. Color: Close to 146A.

*Reproductive organs.*—Androecium: Stamen quantity per flower: Numerous, about 100. Anther shape:

Reniform. Anther size: About 2 mm by 1.5 mm. Anther color: Close to 4C. Amount of pollen: Moderate. Pollen color: Close to 6A. Gynoecium: Pistil quantity per flower: One with five stigmas. Pistil length: About 3 cm. Style length: About 2.4 cm. Style color: Close to 60A; towards the base, close to 155D. Stigma shape: Rounded. Stigma color: Close to 185B. Ovary color: Close to 144B to 144C.

*Seed/fruit.*—Seed and fruit production has not been observed.

Garden performance: Plants of the new *Hibiscus* have been observed to be tolerant to wind and rain and to have excellent garden performance.

Hardiness: Plants of the new *Hibiscus* have been observed to be hardy to USDA Zone 5.

High temperature tolerance: Plants of the new *Hibiscus* have been observed to tolerate temperatures of about 40° C.

Disease/pest resistance: Plants of the new *Hibiscus* have not been observed to be resistant to pathogens and pests common to *Hibiscus*.

It is claimed:

1. A new and distinct *Hibiscus* plant named 'Splash Yopinot Noir', as illustrated and described.

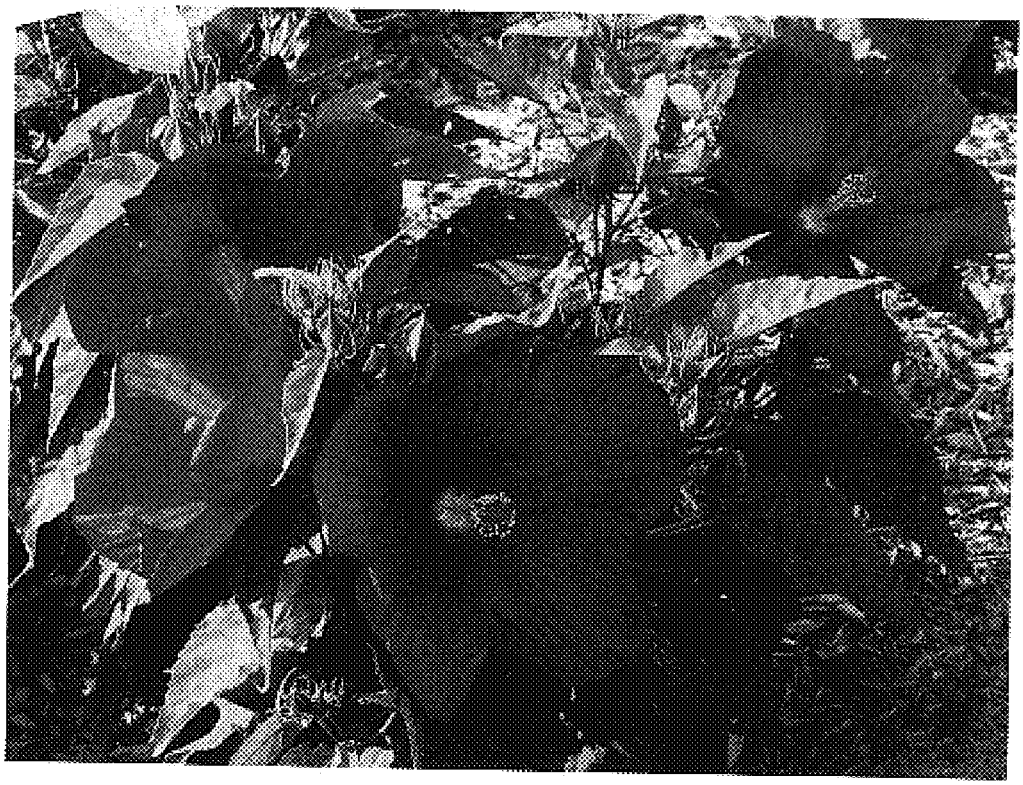

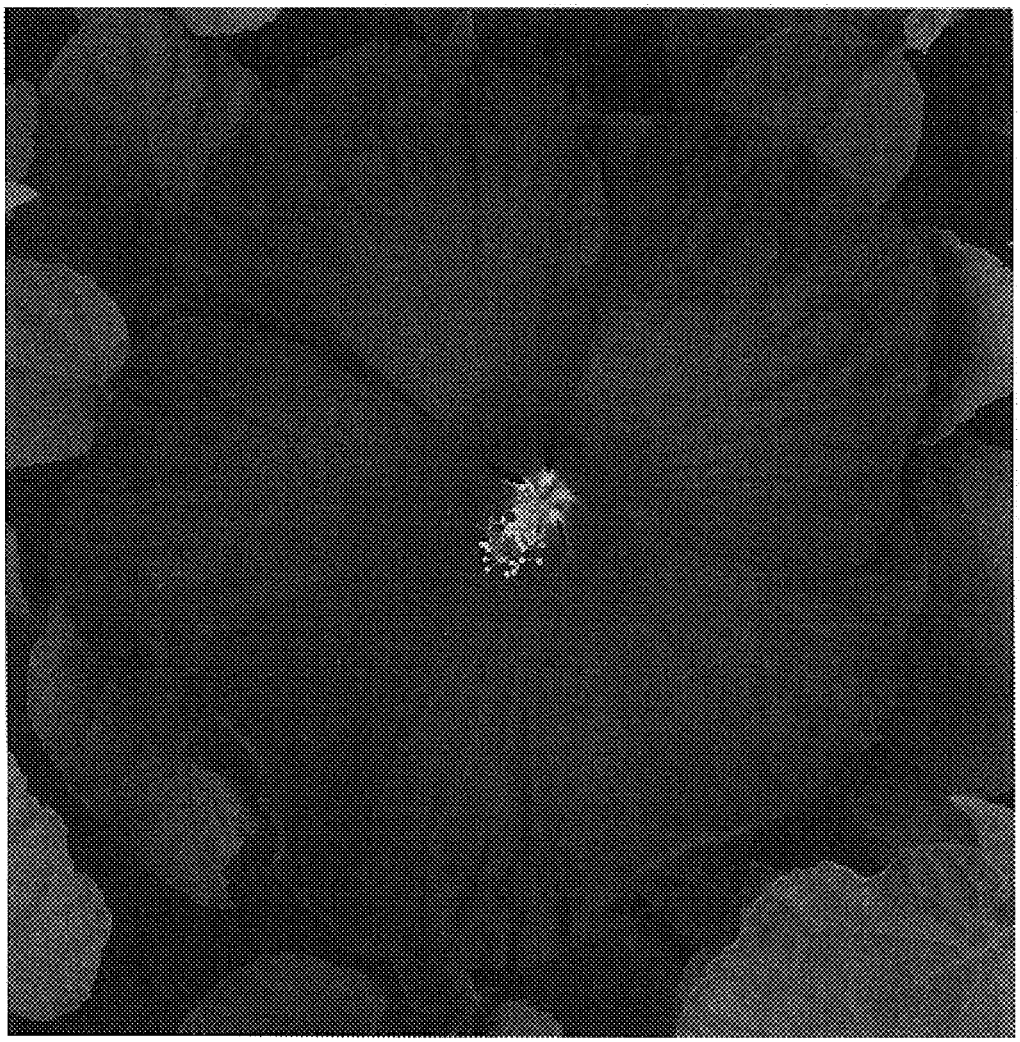

* * * * *